United States Patent [19]

Svadjian et al.

[11] Patent Number: 4,674,496

[45] Date of Patent: Jun. 23, 1987

[54] DOUBLE-LUMEN TUBE ADAPTOR

[75] Inventors: Edward Svadjian, Yonkers; Paul L. Goldiner, Larchmont, both of N.Y.

[73] Assignee: Albert Einstein College of Medicine of Yeshiva University, Bronx, N.Y.

[21] Appl. No.: 913,493

[22] Filed: Sep. 30, 1986

[51] Int. Cl.[4] .......................................... A61M 16/00
[52] U.S. Cl. ................... 128/207.16; 128/912; 128/205.24; 128/4; 604/32; 604/248; 604/256; 137/625.17; 137/625.46; 137/883; 137/887
[58] Field of Search ...................... 128/207.18, 207.16, 128/207.15, 207.14, 200.19, 203.22, 204.18, 204.25, 205.24, 912, 4; 137/625.17, 625.19, 625.24, 625.47, 625.46, 883, 887; 604/32, 248, 256

[56] References Cited

U.S. PATENT DOCUMENTS

| | | | |
|---|---|---|---|
| 811,111 | 1/1906 | Wegefarth | 604/32 |
| 1,607,726 | 11/1926 | De Suszko | 604/32 |
| 1,658,754 | 2/1928 | Wood | 604/32 |
| 2,854,027 | 9/1958 | Kaiser et al. | 604/248 |
| 3,791,379 | 2/1974 | Storz | 137/625.47 |
| 4,489,721 | 12/1984 | Ozaki et al. | 128/205.24 |
| 4,595,005 | 6/1986 | Jinotti | 128/207.16 |

Primary Examiner—Henry J. Recla
Attorney, Agent, or Firm—Amster, Rothstein & Ebenstein

[57] ABSTRACT

Double-lumen tube adaptors for use with either single or dual anesthesia or ventillating machines enable the various features thereof to be utilized without airway disconnection or clamping, interruption of ventilation or the use of unreliable mechanical elements. The adaptor having a single machine-side entry port comprises a support frame and a pair of linear axially-extending cylindrical tubes in substantially parallel disposition extending rotatably through the frame, each of the tubes defining externally of the frame at one end a patient-side exit port adapted for communication with a patient via one lumen of a double-lumen tube and at the other end an entry port with a removable cap. Each of the tubes further defines within the frame interior intermediate the entry and exit ports an aperture extending appreciably in a direction transverse to the tube axes. A machine-side common entry port extends partially through the frame and is adapted for communication at a first or external end with an anesthesia or ventillating machine and adjacent a second or internal end with both of the tubes adjacent the tube apertures, the degree of communication between the common entry port second end and each of the tube apertures being a function of the rotational disposition of the respective tube.

7 Claims, 8 Drawing Figures

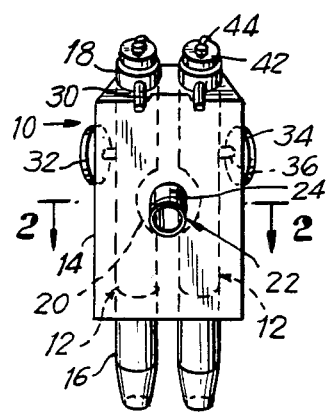
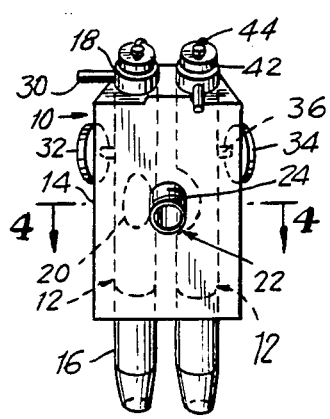
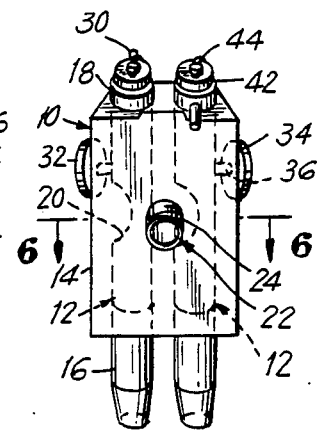
FIG. 1   FIG. 3   FIG. 5
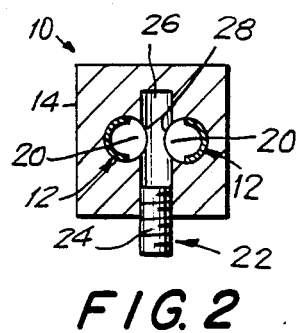
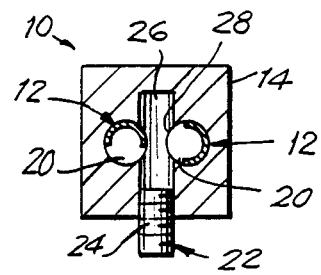
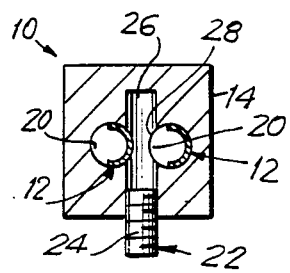
FIG. 2   FIG. 4   FIG. 6

DOUBLE-LUMEN TUBE ADAPTOR

BACKGROUND OF THE INVENTION

The present invention relates to means for connecting a patient to an anesthesia or ventilating machine, and more specifically to a double-lumen tube adaptor which permits such connection while providing advantages not heretofor attainable.

Once a patient is fitted with a double-lumen or two passageway tube, the connection between the double-lumen tube and the anesthesia machine or ventilator is typically made through an adaptor referred to as a double-lumen tube adaptor. Detailed study and investigation of previously designed double-lumen tube adaptors has revealed the tremendous need for a simple adaptor allowing conventional ventilation of both lungs with several desired features:

(1) The ability to ventilate each lung independently;
(2) The ability to expose one lung to atmospheric pressure;
(3) The ability to suction each lung independently;
(4) The ability to sigh each lung independently;
(5) The ability to perform fiberoptic bronchoscopy on each lung independently.

At the same time modern respiratory therapy implies the need for a second simple adaptor allowing several additional features:

(6) The ability to apply one-lung PEEP (Positive End-Expiratory Pressure) or CPAP, with or without tidal ventilation;
(7) The ability to apply differential PEEP to both lungs;
(8) The ability to deliver simultaneous independent lung ventilation.

While the first five features are obtainable with a double-lumen tube adaptor of a first type having only a single or common machine-side entry port (that is, a machine-side port connecting with but a single anesthesia machine or ventilator), the last three features (in addition to the first five) are obtainable only with a second type of double-lumen tube adaptor, one having two independent machine-side entry ports (that is, separate machine-side entry ports for connection to separate anesthesia or ventilating machines).

The prior art double-lumen tube adaptors of both types have not proven entirely satisfactory in use. For example, their design is typically so complex as to require airway disconnection or clamping, interruption of ventilation, or the use of unreliable mechanical elements to enable switching from one feature to another. In particular, the complexity of the design of the adaptor having a machine-side common entry port (type one) described in Yamamura T., "A Single-Unit Device For Differential Lung Ventilation with only one anesthesia machine." *Anesthesia and Analgesia*, 64:1017-20 (1985), is so complex as to require internally both stopcocks and a one-way valve. The adaptor with two machine-side entry ports (for two anesthesia machines or ventilators) (type two) described in Andersen H. W., "A New Improved Double-Lumen Tube Adaptor," *Anesthesiology*, 56:54-56 (1982) similarly requires the use of unreliable stopcocks.

Accordingly, it is an object of the present invention to provide a double-lumen tube adaptor having all of the requisite features of its type (as described above) and affording use of all of these features without airway disconnection or clamping, interruption of ventilation, or the use of unreliable mechanical elements.

It is another object to provide such an adaptor having a high degree of reliability in use through the absence therefrom of valves, stopcocks and other inherently unreliable mechanical elements.

A further object is to provide such an adaptor which is economical to manufacture and maintain due to its simplified design.

SUMMARY OF THE INVENTION

It has now been found that the above and related objects of the present invention are obtained in a pair of double-lumen tube adaptors according to the present invention, one of each type.

The adaptor of the first type, having a single or common machine-side entry port, comprises a support frame and a pair of linear axially-extending tubes in substantially parallel disposition extending through the frame. Each of the tubes defines external to the frame at one end a patient-side exit port adapted for communication with the patient and at the other end an entry port, with each of the tubes further defining within the frame interior intermediate the entry and exit ports an aperture extending appreciably in a direction transverse to the tube axis. Separate closure means are mounted on each of the entry ports and independently movable between a first position closing the respective entry port and a second position opening the respective entry port. Separate means are secured to each of the tubes for independently rotating the respective tube about its axis relative to the frame, with separate locking means for each of the tubes being provided for independently locking the respective tube against such rotation. A machine-side common entry port extends partially through the frame and is adapted for communication at a first or external end with an anesthesia or ventilating machine and adjacent a second or internal end with each of the tubes adjacent the tube apertures. The degree of gaseous communication between the common entry port's second end and each tube aperture is a function of the rotational disposition of the respective tube.

Preferably the common entry port extends through the frame substantially perpendicular to the tube axes, typically the common entry port extending substantially horizontally and the tubes extending substantially vertically.

The tubes and the common entry port have substantially cylindrical external countours, with the common entry port defining adjacent each tube an aperture adapted to receive an accurate segment of the tube in an air-tight relationship. The apertures of the common entry port and the tubes are configured and dimensioned to enable the communication between the common entry port and each of the tubes to be smoothly varied between zero and one-hundred percent of the maximum communication. To enable this variation with only a 180-degree rotation of the tube, each of the tube apertures extends in the circumferential direction of the respective tube between 25 and 50 percent of the circumferential length.

According to the present invention, the double-lumen tube adaptor of the second type, having a pair of machine-side entry ports, comprises a support frame and a pair of linear tubes extending through the frame. Each of the tubes defines a patient-side exit port external to the frame at one end adapted for communication with a patient and external to the frame at the other end an entry port, each tube further defining an aperture within the frame interior intermediate the entry and exit ports. Separate closure means are removably mounted on each of the entry ports and independently movable between a first position closing the respective entry port and a second position opening the respective entry port. A machine-side entry port for each of the tubes extends partially through the frame and is adapted for communication at a first or external end with an anesthesia or ventilating machine and at a second or internal end with a respective tube aperture.

Preferably a septum is disposed within the frame to effectively divide the frame into two air-tight compartments, each compartment containing portions of only one of the tubes and only one of the machine-side entry ports.

BRIEF DESCRIPTION OF THE DRAWING

FIG. 1 is a perspective view of a double-lumen tube adaptor of the first type having a single machine-side entry port, according to the present invention, with both tubes being oriented for maximum flow therethrough;

FIG. 2 is a sectional view taken along the line 2—2 of FIG. 1;

FIG. 3 is a perspective view of the adaptor of FIG. 1, but with the left-hand tube being rotated 90 degrees to reduce the flow therethrough from the machine-side entry port by 50 percent;

FIG. 4 is a sectional view taken along the line 4—4 of FIG. 3;

FIG. 5 is a perspective view of the adaptor of FIG. 1, but with the left-hand tube being rotated 180 degrees to terminate flow therethrough from the machine-side entry port;

FIG. 6 is a sectional view taken along the line 6—6 of FIG. 5;

DETAILED DESCRIPTION OF THE PREFERRED EMBODIMENTS

Figure 7:
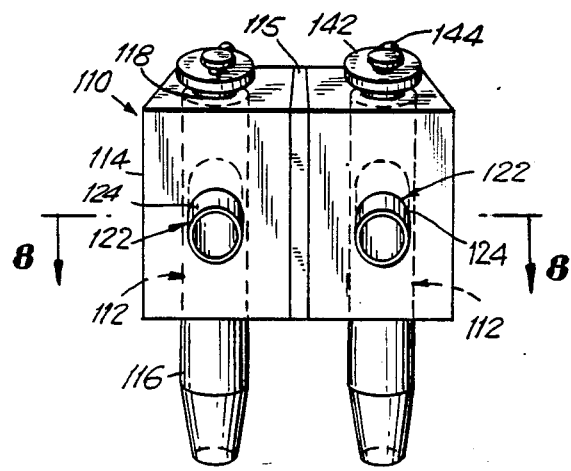
FIG. 7 is a perspective view of a double-lumen tube adaptor of the second type having a pair of machine-side entry ports, according to the present invention.

Referring now to the drawing, and in particular to FIGS. 1-6 thereof, therein illustrated is a first embodiment of the present invention, a double-lumen tube adaptor of the first type having a single machine-side entry port, generally designated by the numeral 10. Two linear axially-extending cylindrical tubes, generally designated by the numeral 12, extend vertically in substantially parallel disposition through opposed ends of a support frame 14. Each tube 12 is mounted on frame 14 for rotation about its axis relative to the frame and defines at the bottom end below the frame, a patient-side exit port 16 adapted for communication with the patient via one lumen of a conventional double-lumen tube (not shown) and at the top end, above the frame, an entry port 18. Each tube 12 further defines within the frame 14, intermediate the entry and exit ports 18, 16, an aperture 20 extending appreciably in a direction transverse to the tube axis, and preferably between 25 and 50 percent of the circumferential length of the tube, at least at the widest point of the tube aperture 20.

A single machine-side common entry port, generally designated by the numeral 22, extends partially through the frame 14 and is adapted for communication, at a first or external end extending forwardly from the frame 14, by a male connector 24, with an anesthesia or ventilating machine (not shown) and, adjacent a second or internal end 26 within the interior of frame 14, with both of the tubes 12 adjacent the tube apertures 20. The common entry port 22 extends through the frame 14 substantially perpendicular to the axes of the tubes 12, the latter typically extending substantially vertically and the former therefore extending substantially horizontally. Like the tubes 12, the common entry port 22 has a substantially cylindrical external contour, but defines adjacent each tube 12 an aperture 28 adapted to receive an arcuate segment of the tube 12 in an air-tight relationship. While the frame 14 is preferably of solid air-impermeable construction throughout, as shown, alternatively it may be of hollow construction with merely sufficient internal structure to provide an air-impermeable seal about the tube apertures 20 and the common entry port apertures 28.

The tubes 12 are provided, adjacent the entry ports 18 above the top of frame 14, with rotating means, such as handles 30, for independently rotating each of the tubes about its axis relative to the frame 14. The apertures 28 and 20 of the common entry port 22 and tubes 12, respectively, are configured and dimensioned to enable the gaseous communication between the common entry port 22 and each of the tubes 12 to be smoothly varied between zero and one-hundred percent of the maximum communication simply by rotating the handle 30 of a tube from its forwardly pointing position (corresponding to 100% communication) through its outwardly laterally extending position (corresponding to approximately 50 percent of the maximum communication) to a rearwardly pointing position (representing zero communication). A stop (not shown) may be provided to limit tube rotation, preferably to 180 degrees.

Separate locking means, generally designated by the numeral 32, are provided for each of the tubes 12 for independent locking of that tube against rotation about its axis relative to the frame 14, and hence for maintaining the given level of communication between the tube aperture 20 and the common entry port aperture 28. More specifically, the locking means 32 comprises a locking wheel 34, rotatably mounted on the side of the frame 14 adjacent to tube 12 in question, and an integral locking shaft or pin 36 in threaded engagement with a horizontal aperture extending inwardly from the frame side towards the outer surface of the tube so that appropriate rotation of locking wheel 34 drives the inner end of pin 36 inwardly so as to abut against the particular tube 12 and preclude rotation thereof.

Finally, a separate closure means, such as a cap 42, is seated on each of the entry ports 18 to independently close the same. The caps 42 may be independently manually removed from either entry port 18 in order to open the ports and thereby, for example, expose a given lung to atmospheric pressure, suctioning or fiberoptic bronchoscopy (the latter being performable straight down the uncapped linear tube 12). As removal of the cap 42 results in one hundred percent collapse of the lung in question, the corresponding tube 12 should be in the closed or zero percent communication position prior to cap removal so as to allow passage of the entire tidal volume from the common entry port 22 through the other tube 12 into the other lung of the patient. In order to prevent loss of the removed cap 42, each cap 42 is secured to the frame 14 by a connector 44, such as a wire.

While the precise dimensions of the external or male connector 24 of the common entry port 22 and the exit port 16 of the tubes 12 will, of course, depend on the leads from the given anesthesia machine or ventilator, in the first case, and the two lumens of the double-lumen tube, in the second case, generally a fifteen-millimeter male connector 24 and exit ports of eight millimeters ID are satisfactory.

Progressive collapse of the left lung (or more precisely, that lung associated with the left exit part 16 of the adaptor 10) is shown in the sequence of FIGS. 1 and 2 (no collapse), through FIGS. 3 and 4 (fifty percent collapse, with the rest of the flow going to the right lung), and FIGS. 5 and 6 (with total collapse of the left lung). Referring now to FIGS. 1 and 2, when both handles 30 are facing in the forward direction, there is maximum gaseous communication between the common entry port apertures 28 and each of the tube apertures 20 so that the entire flow of the anesthesia machine or ventilator through the common entry port 22 is equally divided between the two tubes 12 and hence the two exit ports 16. In FIGS. 3 and 4, the left handle 30 has been rotated outwardly 90 degrees, so that the left tube 12 has been similarly rotated and the degree of communication between the common entry port aperture 28 and the tube aperture 20 has been reduced in the case of the left tube by about 50 percent. Referring now to FIGS. 5 and 6, the left handle 30 has been rotated a further 90 degrees (so it now faces the rear of the adaptor) so that the left tube 12 has been rotated correspondingly and there is no longer any communication between the common entry port aperture 28 and the left tube aperture 20. Needless to say, prior to each rotation of either tube 12, the appropriate locking wheel 34 should be rotated in the opening direction to release the locking pin 36 from the tube to be rotated and, after tube rotation, the locking wheel should be rotated in the opposite direction to cause re-engagement of the locking pin with the tube to fix the tube orientation.

Figure 8:
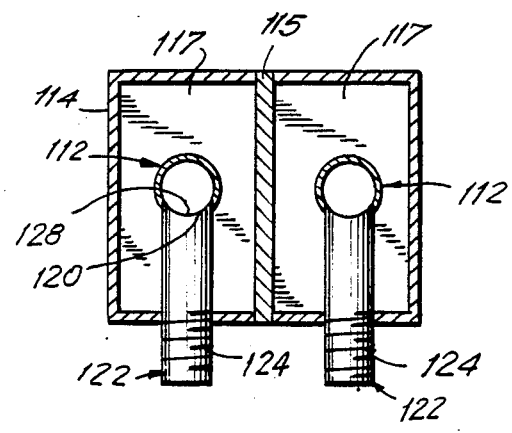
FIG. 8 is a sectional view taken along the line 8—8 of FIG. 7.

Referring now to FIGS. 7 and 8, therein illustrated is a second embodiment of the present invention, a double-lumen tube adaptor having a pair of machine-side entry ports for use with a pair of anesthesia machines or ventilators, generally designated by the numeral 10. In designating the elements of this embodiment 110, the drawing elements will be identified by three-digit numerals with the last two digits corresponding, where appropriate, to roughly functionally similar elements of the first embodiment.

As a primary difference between the first and second embodiments is the inability of the tubes 112 to rotate in the second embodiment 110, clearly there is no need for either the rotating means 30 or the locking means 32 of the first embodiment 10. Furthermore, as the connection between the machine-side entry ports 122 (and apertures 128) and the tubes 112 (and apertures 120) are fixed, there is no need for the frame 114 to be air-tight about the intersection of machine-side entry port aperture 128 and tube aperture 120 provided there is a septum or divider 115 dividing the frame 114 into two air-tight compartments 117, each compartment containing portions of only one tube 112 and only one machine-side entry port 122.

To use the adapter 110, the male connectors 124 of the machine-side entry ports 122 are connected to the female leads (not shown) of a pair of anesthesia machines or ventilators. Similarly, the exit ports 116 of the tubes 112 are connected to the lumens (not shown) of a double-lumen tube. Gas flow from a given machine passes through one of the machine-side entry ports 122 and its aperture 124 in a given compartment 117, and hence to the tube 112 and its aperture 120 in that compartment 117, finally emerging from the exit port 116 of the compartment 117 into the appropriate lumen of a double-lumen tube. For exposure of a lung to atmosphere, suctioning, or fiberoptic bronchoscopy, the appropriate cap 142 is simply removed from the appropriate tube entry port 118.

While the second embodiment of the present invention requires the use of a pair of anesthesia machines or ventilators, it enables one to utilize all the features thought to be desirable in association with a double-lumen tube adaptor.

To summarize, the present invention provides a simple adaptor enabling various one-lung functions without requiring interruptions of the ventilation of the other lung or the use of any clamps to the airway tubing. Since suctioning or fiberoptic bronchoscopy can be performed through straight pathways, kinking or bending of the bronchoscope or suction tube cannot occur. Similarly, as no clamps are required, there is no possibility of damage to the double-lumen tube by crush injury from an external clamp. Furthermore, the adaptor avoids any of the mechanical devices likely to go awry such as valves and stopcocks. Finally, the simplified design of the adaptor enables it to be manufactured and maintained economically.

Now that the preferred embodiments of the present invention have been shown and described in detail, various modifications and improvements thereon will become readily apparent to those skilled in the art. Accordingly, the spirit and scope of the present invention is to be limited only by the appended claims, and not by the foregoing specification.

What is claimed is:

1. A double-lumen tube adaptor having a single machine-side entry port comprising:
   (a) a support frame;
   (b) a pair of linear axially-extending cylindrical tubes in substantially parallel disposition extending through said frame, each of said tubes defining at one end a patient-side exit port adapted for communication with a patient via one lumen of a double-lumen tube and at the other end an entry port, each of said tubes further defining intermediate said entry and exit ports an aperture extending appreciably in a direction transverse to said tube axis;
   (c) separate closure means mounted on each of said entry ports and independently movable between a first position closing said respective entry port and a second position opening said respective entry port;
   (d) separate means secured to each of said tubes for independently rotating said respective tube about its axis relative to said frame;
   (e) separate locking means for each of said tubes for independently locking said respective tube against rotation about its axis relative to said frame; and
   (f) a machine-side common entry port extending partially through said frame and adapted for communication at a first end with an anesthesia or ventilating machine and adjacent a second end with both of said tubes adjacent said tube apertures, the degree of communication between said common entry port second end and each of said tube apertures being a function of the rotational disposition of the respective tube.

2. The adaptor of claim 1 wherein said common entry port extends through said frame substantially perpendicularly to said tube axes.

3. The adaptor of claim 2 wherein said tubes extend substantially vertically and said common entry port extends substantially horizontally.

4. The adaptor of claim 1 wherein each of said tube apertures extends in the circumferential direction of said respective tube between 25 and 50% of the circumferential length.

5. The adaptor of claim 1 wherein said tubes and said common entry port have substantially cylindrical external contours, and said common entry port defines adjacent each tube an aperture adapted to receive an arcuate segment of said tube in an air-tight relationship.

6. The adaptor of claim 5 wherein said frame is air-impermeable about said apertures of said tubes and said common entry port.

7. The adaptor of claim 5 wherein said apertures of common entry port and said tubes are configured and dimensioned to enable the communication between said common entry port and each of said tubes to be smoothly varied between 0 and 100% of the maximum communication.

* * * * *